United States Patent [19]

Fiorenzano, Jr.

[11] Patent Number: 4,877,990
[45] Date of Patent: Oct. 31, 1989

[54] STERILIZATION SYSTEM BY MEANS OF HIGH THERMAL GRADIENT DUCTS

[76] Inventor: Alintor Fiorenzano, Jr., Rua Marechal Deodoro, No. 195/214,, Cep: 25600 - Petropolis - RJ, Brazil

[21] Appl. No.: 29,986

[22] Filed: Mar. 25, 1987

Related U.S. Application Data

[63] Continuation-in-part of Ser. No. 683,520, Dec. 19, 1984.

[51] Int. Cl.⁴ ............................ F24H 3/00; H05B 1/00
[52] U.S. Cl. ..................................... 219/381; 219/374
[58] Field of Search ................. 219/374, 375, 382, 381

[56] References Cited

U.S. PATENT DOCUMENTS

| | | | |
|---|---|---|---|
| 3,349,224 | 10/1967 | Jaeger | 219/374 |
| 3,541,304 | 11/1970 | Cohn | 219/374 |
| 3,654,432 | 4/1972 | Dyre | 219/374 |
| 4,233,494 | 11/1980 | Paulik et al. | 219/382 |
| 4,536,642 | 8/1985 | Hamster et al. | 219/381 X |

Primary Examiner—E. A. Goldberg
Assistant Examiner—M. M. Lateef

[57] ABSTRACT

An air sterilizer comprises a block of insulative material having therethrough a plurality of small diameter ducts provided with axially disposed resistive heating elements which generate high thermal gradients within the ducts to eliminate micro-organisms passing through the same. Total energy consumption is in the range of 14–25 Watts.

5 Claims, 2 Drawing Sheets

STERILIZATION SYSTEM BY MEANS OF HIGH THERMAL GRADIENT DUCTS

CROSS-REFERENCE TO RELATED APPLICATIONS

This is a Continuation-In-Part of application Ser. No. 683,520 filed Dec. 19, 1984.

BACKGROUND OF THE INVENTION

The present invention relates to an improved apparatus utilizing the effect caused by the passage of a continuous air flow through a relatively large number of electrically heated small diameter ducts in which energy is dissipated by the Joule effect and wherein the high thermal gradient as produced in the interior of the ducts exhibits an average value of 220° C. such that the protein membrane associated with most bacteria and virus found in the air is destroyed.

The concept of employing thermal effect as a sterilizing agent is generally well known, as is also the idea that the Joule effect may be used as a heating source. Examples of prior devices for cleaning or purifying air by means of an elongated or tubular passageway associated with heating means will be found in U.S. Pat. Nos. 2,014,455, 2,564,898 and 3,691,346. Such devices either require the consumption of a relatively high amount of current, emit a concentrated air flow and/or result in the discharge of air at a noticeably elevated temperature. Until the instant invention, thermal processes for obtaining air sterilization, without using electrostatic or catalytic devices, have resulted in the significant heating of the ambient air.

Presently, several methods are employed to achieve air sterilization in situations where the proliferation of micro-organisms is high. The most common methods include the direct use of Joule effect by simple heating or by incandescent bulbs. This does not present any improvement of a thermodynamic nature and thus exhibits low efficiency as far as the sterilization effect is concerned. An additional method has been the use of ultra-violet radiation in forced air-flow chambers.

SUMMARY OF THE INVENTION

The present invention introduces as a novel approach the employment of an insulative or refractory block, provided with a plurality of high thermal gradient ducts arranged to enhance the sterilizing action of the Joule effect thus improving its efficiency in the destruction of micro-organisms present in the air, without causing noticeable ambient air temperature elevation in rooms where the device is installed.

The underlying technical-scientific principle on which this system rests is thermodynamics, involving the convection of gases through a relatively large number of closely arranged, vertically aligned, axially-heated ducts of small diameter. Each of the ducts is preferably heated by means of a low wattage (i.e., 15–25 W) resistance wire disposed within its core.

The advantages of the present invention over prior processes include: an increase in efficiency in terms of the sterilized volume of air per watt consumed which is due to the high thermal gradient ducts provided with axially disposed heating means; and simplicity of the heating process, since high efficiency is attained by a select choice of the duct parameters according to the laws of thermodynamics.

This invention has a wide variety of applications, particularly those which require elimination of micro-organisms found in the air in indoor situations, such as hospital operating and patient rooms or in other enclosures requiring modification of the relative humidity of the air, without causing considerable modification of the ambient temperature. The present arrangement can be readily adapted to accommodate any air volume in view of a very well defined correlation between the air volume and power of the device. An extremely small, portable embodiment of the invention, not requiring any mechanical propulsion of the air, has been found to satisfactorily sterilize the air in thousands of hospital installations, resulting in a vastly improved environment, particularly beneficial for those prone to respiratory illnesses. Experience has shown that with the present apparatus, 2.5 cubic meters of air per hour can be sterilized with a power consumption of only 25 W/hr as opposed to prior devices using a minimum of 1.5 KW/hr for the treatment of the same volume of air.

According to measurements taken with prototypes of the instant device functioning at their ideal operating level, a consumption of 5 watt-hour/cubic meter was observed, with the resultant air having a negligible amount of micro-organisms. When these results are compared with those associated with the use of incandescent bulbs, a factor of 20 can be observed, that is, for the same initial amount of micro-organisms in the air, a sterilizing system using incandescent bulbs requires 100 watt-hour/cubic meter in order to achieve a negligible amount of micro-organisms in the air.

Taking into account the above experimental results, it can be concluded that the sterilization system based upon high thermal gradient ducts acted upon by the Joule effect is highly efficient when compared with existing alternatives. The Joule effect in this system can be produced by the passage of an electric current through a resistive element such as a NiCr wire axially disposed in ducts designed to benefit from thermodynamic principles. This axial disposition as opposed to a helical filament, not only reduces the amount of filament needed for each duct but also minimizes obstruction of air flow by convection through the ducts.

Accordingly, one of the objects of the present invention is to provide an improved air sterilization apparatus including a plurality of small diameter ducts electrically heated and arranged to dissipate energy by the Joule effect while producing a high thermal gradient.

Another object of the present invention is to provide an improved air sterilization apparatus including a plurality of small diameter ducts each heated by a low-wattage resistance element producing a value of over 200° C. within the ducts without significantly elevating the surrounding air.

A further object of the present invention is to provide an improved air sterilization apparatus including a plurality of small diameter ducts, internally electrically heated and vertically disposed to achieve passage of air therethrough solely by convection.

With these and other objects in view which will more readily appear as the nature of the invention is better understood, the invention consists in the novel construction, combination and arrangement of parts hereinafter more fully described, illustrated and claimed, with reference being made to the attached drawings.

DESCRIPTION OF THE PREFERRED EMBODIMENT

Figure 1:
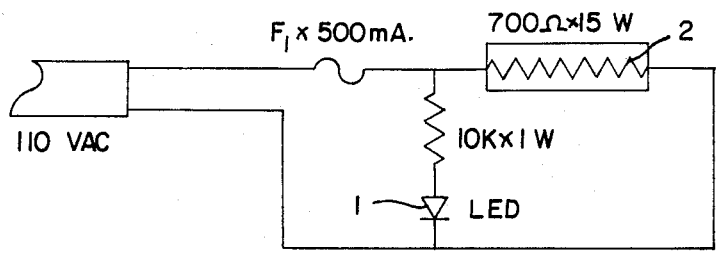
FIG. 1 is schematic of a typical electrical system used with the device of this invention.

FIG. 1 is a diagram of a preferred electrical arrangement as used in the present system and will be seen to include a fuse $F_1$ for protection of the device, an LED (Light Emitting Diode) 1 serving as an on-off indicator and one of a plurality of heating elements 2, made of NiCr resistive wire filament whose electrical characteristics are selected in order to suit the air volume to be sterilized. A typical installation according to the present invention uses wire filament having a resistance of 100 ohm/meter, and wherein a plurality of straight or axially extending filaments are employed, each comprising a length of 70 millimeters.

Figure 2:
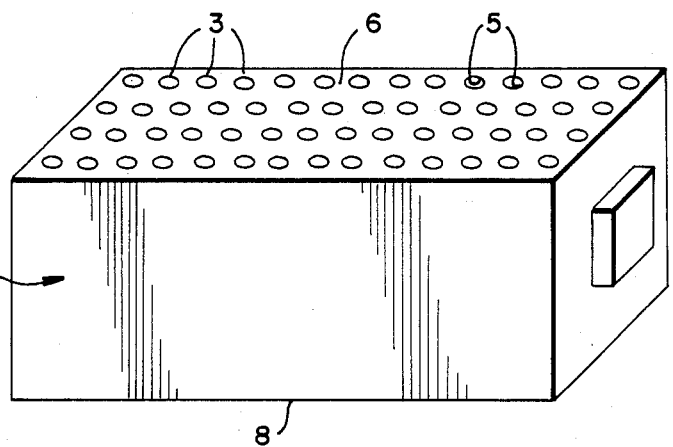
FIG. 2 is a top perspective view of the insulative block of the sterilization apparatus, shown without the electrical heating elements installed.

FIG. 2 shows the top view of a plurality of vertically extending high thermal gradient ducts 3 which are also designed as a function of the air volume to be processed. These ducts 3 are formed as bores extending throughout the entire height of an insulative or refractory mass or block 4 in order to maximize heat transfer to the air which automatically will be drawn therethrough. It will be understood that air within an enclosure equipped with this invention will circulate upwardly through the ducts 3 solely by convection in view of the heat generated therein by the elements 2 in each duct. With the disclosed arrangement, utilizing 15 Watt 700 OHM heating elements 2 driven by 110 VAC, it will be understood that in a typical system, including 56 ducts 3 as shown, no more power than 25 Watts will be consumed.

Figure 3:
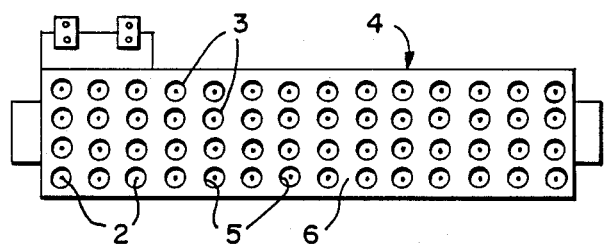
FIG. 3 is a top plan of FIG. 2, with heating elements shown in the duct cores.

FIG. 3 shows a top view of the high thermal gradient duct system. From this view, the ducts 3 will be seen to comprise a circular cross-section but any other geometric form can be alternatively used. Each duct 3 includes an uppermost top end 5 associated with a top 6 of the refractory block 4. The individual heating elements 2 will be understood to comprise single, straight filaments extending axially within each duct 3.

The plurality of elements 2 are connected in series outside one or the other end of the respective ducts 3 as is well known. For purposes of clarity these connections are omitted in the drawings.

Figure 4:
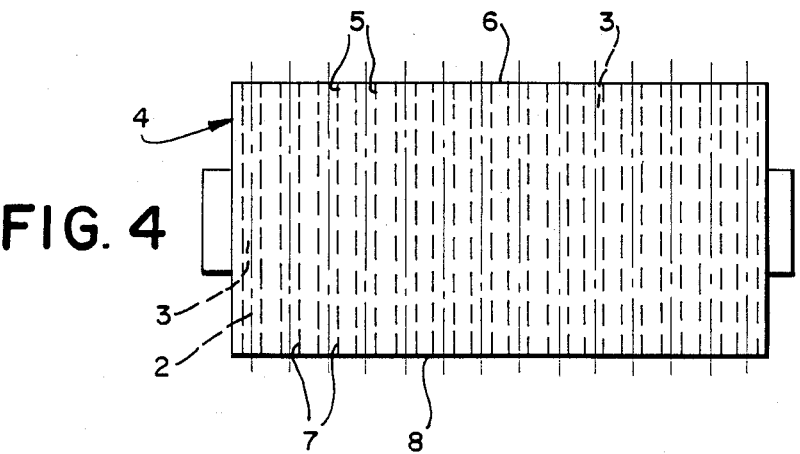
FIG. 4 is a front elevation of FIG. 3.

FIG. 4 shows a frontal view of the above-mentioned system of ducts 3 through the block 4 and their vertical, axial disposition through the block. The lowermost or bottom end 7 of the ducts 3 will be seen to open through the bottom 8 of the block 4.

Figure 5:
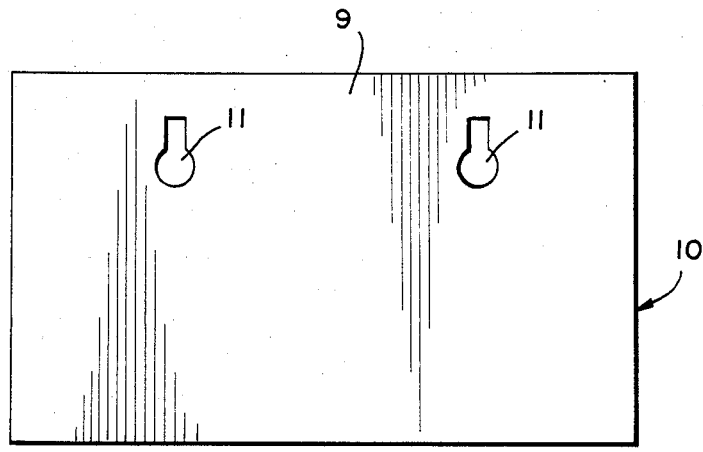
FIGS. 5, 6 and 7 are respectively rear, front and bottom views of the case containing the insulative block of the invention.

FIG. 5 shows the back 9 of an aluminum box or case 10 adapted to house the block 4 shown in FIGS. 2–4. Suitable mounting means such as the illustrated keyhole cut-outs 11 may be provided to allow mounting of the system, such as on a wall of an enclosure.

Figure 6:
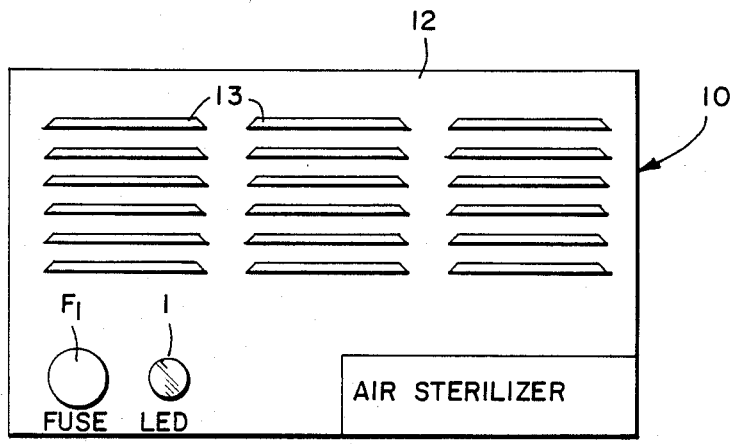
Figure 7:
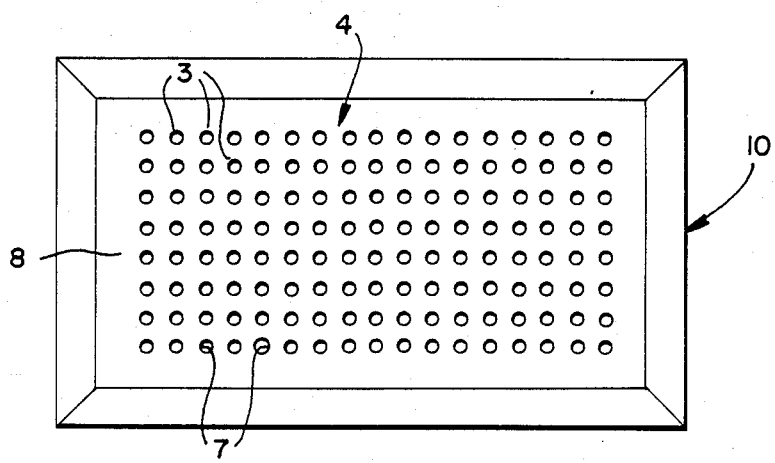

FIGS. 6 and 7 show respectively the front and bottom views of the apparatus. The box front 12 includes louvers 13 facilitating dissipation of heat from the block 4 housed in the box and conveniently displays the fuse $F_1$ and LED 1. Sides 9'—9' join the box front 12 to the back 9. The box bottom 14 shown in FIG. 7 may comprise a plurality of inwardly directed flanges serving to support the block 4 while allowing full communication between the ambient air and the bottom ends 7 of the ducts 3.

The outstanding efficiency of the instant apparatus is attributable to the constriction of the air into extremely small volumes as it passes by convection upwardly through the ducts 3 in the thermal and electrical insulating material of the block 4. The refractory block is preferably formed of $ZrO_2$ and $SiO_2$ and, as shown in the illustrated embodiment, includes a substantial number of the relatively closely disposed bores or ducts 3 formed therein, in a vertical manner. The illustrated apparatus is formed with a total of 56 such ducts 3 but obviously larger or smaller blocks 4 may be used, having a correspondingly greater or lesser number of ducts. In any case, the respective ducts 3, which actually perform in a manner similar to capillary tubes in receiving, vertically advancing and discharging the ambient air, each measure substantially 2 mm in diameter in a block which has a height of approximately 70 mm.

The appropriate heating, convection and sterilization of air as treated by the disclosed apparatus has been found to result by utilizing heating elements 2 of NiCr filament rated at 100 Ohms/meter, with a single axial length (70 mm) of this filament thus being employed within each duct. Including the extra filament used to join the plurality of elements 2 within the ducts (omitted from the drawings for clarity), it will be understood that approximately 4.5 meters of filament are involved in the apparatus. With a supplied voltage of 110 this will translate into a power consumption of 24.4 Watts.

The power dissipated by Joule effect in each centimeter of heating element 2 is calculated as:

$$\text{Total } P/\text{filament length} = 24.4 \div 450$$
$$= 0.0542 \text{ W/cm}$$

Using this value and applying it to the length of each duct (7 centimeters) it will be seen that the power dissipated within each duct is 0.38 Watt. The volume of air contained in each 2 mm diameter duct is calculated as follows:

$$\text{Diameter} = 2 \times 10^{-3} \text{ meter}$$
$$\text{Height} = 7 \times 10^{-2} \text{ meter}$$
$$\text{Duct vol.} = \frac{\pi}{4} \times 7 \times 10^{-2} \times (2 \times 10^{-3})^2 \text{ cubic meter}$$
$$= 2.2 \times 10^{-7} \text{ cubic meter}$$

The very high power density within each duct, in Watt/cubic meter is calculated as dissipated power per duct divided by duct volume as below:

$$0.38 \text{ Watt} \div 2.2 \times 10^{-7} \text{ cubic meter} =$$
$$1.7272 \times 10^6 \text{ Watt/cubic meter}$$

In an abiabatic system such a density of dissipated power in one cubic meter of air under normal conditions of temperature and pressure, for one second, could raise the temperature to more than 900° C. By contrast, with the present invention, the temperature reached within the ducts is at most 400° C., considering a normal ambient temperature of 24° C. and relative humidity of 80%. Under these conditions, the average time air remains in each duct will be 0.4 seconds as this air is subjected to an average speed of 17.5 centimeters per second.

Summarizing he main characteristics of the present apparatus, it will be seen that air sterilization is achieved by means of axially heated high thermal gradient ducts in a manner which differs from the technological contributions available up to this time and wherein:

(1) the apparatus includes a block of thermal and electrical non-conducting material;
(2) this block generates an area of very high power density through the dissipation of low power inside a plurality of small volume ducts;
(3) the external temperature of the refractory material is low; in an apparatus according to that as disclosed herein, this temperature is about 65° C.;
(4) the high power density inside the ducts formed in the refractory material makes air sterilization possible without the use of catalyzers;
(5) it allows the use of the air sterilizer not only in commercial environments but also at home, in any season of the year, as it does not significantly raise the ambient temperature, consumes little energy, and is one alternative to the treatment of allergy diseases.

The application of the invention here discussed is directly related to the optimization of systems suitable for thermal sterilization of the air and can be used in wardrobes, rooms, perishable goods warehouses and in any other place where micro-organism action must be prevented. This system is also highly efficient against mold and bad odors commonly found in wardrobes, attics, cellars, etc. It can also be used in hospitals and clinics where high level biological activity in the air should be kept to a minimum.

I claim:

1. An air sterilization apparatus comprising a refractory block having a top and a bottom, a plurality of vertically disposed ducts extending through said block from said bottom to said top, said ducts having a cross-sectional area of between 1.7–7.07 square millimeters and a length of between 4–12 centimeters, said ducts including top and bottom ends and said duct ends communicating directly with ambient air, an axially extending resistive heating filament disposed within each of said ducts, and means for supplying electrical energy to said heating filaments to produce a high thermal gradient in said ducts whereby ambient air is drawn into and upwardly through said ducts solely by convection with minimal increase in temperature of the ambient air due to air issuing from said ducts.

2. An air sterilization apparatus according to claim 1 wherein the total power consumption of said heating elements is within the range of 12–30 Watts.

3. An air sterilization apparatus according to claim 1 wherein each heating filament comprises NiCr wire.

4. An air sterilization apparatus according to claim 3 wherein said block comprises a composition whose primary ingredients are zirconium dioxide and silica.

5. An air sterilization apparatus according to claim 4 further including a case, said block being insertable in said case with said duct top and bottom ends clear of engagement of the case, and wherein said case includes mounting means permitting attachment of said apparatus in a position elevated from the floor of an enclosure.

* * * * *